(12) United States Patent
Waedekin et al.

(10) Patent No.: US 9,964,523 B2
(45) Date of Patent: May 8, 2018

(54) METHOD AND APPARATUS FOR CONDUCTING PHASED ARRAY TESTING

(71) Applicant: Konecranes Plc, Hyvinkää (FI)

(72) Inventors: Michael Waedekin, Mukwonago, WI (US); Joseph A. Yustus, Hartford, WI (US)

(73) Assignee: KONECRANES GLOBAL CORPORATION, Hyvinkää (FI)

( * ) Notice: Subject to any disclaimer, the term of this patent is extended or adjusted under 35 U.S.C. 154(b) by 324 days.

(21) Appl. No.: 14/317,770

(22) Filed: Jun. 27, 2014

(65) Prior Publication Data

US 2015/0000409 A1    Jan. 1, 2015

Related U.S. Application Data (60) Provisional application No. 61/841,495, filed on Jul. 1, 2013.

(51) Int. Cl.
| | | |
|---|---|---|
| *G01D 21/00* | (2006.01) | |
| *G01N 29/00* | (2006.01) | |
| *G01N 29/265* | (2006.01) | |
| *G01N 29/22* | (2006.01) | |

(52) U.S. Cl.
CPC ......... *G01N 29/265* (2013.01); *G01N 29/225* (2013.01); *G01N 29/226* (2013.01); *G01N 2291/106* (2013.01)

(58) Field of Classification Search
CPC ........... G01N 2291/106; G01N 29/225; G01N 29/226; G01N 29/265; G01D 11/30; G01D 11/245
USPC ....................... 73/625, 626, 866.5
See application file for complete search history.

(56) References Cited

U.S. PATENT DOCUMENTS

| | | | | |
|---|---|---|---|---|
| 4,109,387 A | * | 8/1978 | Matsuoka | ................ G01B 7/31 29/273 |
| 6,446,005 B1 | * | 9/2002 | Bingeman | .......... A63B 24/0021 180/167 |
| 6,981,419 B1 | * | 1/2006 | Hay | ..................... G01N 29/226 73/636 |

(Continued)

FOREIGN PATENT DOCUMENTS

| | | |
|---|---|---|
| EP | 1906182 | 4/2008 |
| JP | 2013068504 | 4/2013 |
| WO | 2012003071 | 1/2012 |

OTHER PUBLICATIONS

International Search Report from the International Searching Authority for Application No. PCT/IB2014/001228 dated Nov. 18, 2014 (5 pages).

(Continued)

*Primary Examiner* — Helen Kwok
*Assistant Examiner* — Nashmiya Fayyaz
(74) *Attorney, Agent, or Firm* — Michael Best & Friedrich LLP (57) ABSTRACT

A system for conducting phased array testing on a vehicle hub includes a guide element having a first end and a second end, a pivot element extending from the second end to couple to the vehicle hub, and a slide element coupled to the guide element. The slide element is movable relative to the guide element between the first end of the guide element and the second end of the guide element. The slide element including an object-receiving aperture to receive a phased array probe element.

20 Claims, 8 Drawing Sheets

(56) References Cited

U.S. PATENT DOCUMENTS

| | | | | |
|---|---|---|---|---|
| 8,333,116 B2* | 12/2012 | Boone | .................. | G01M 13/00 |
| | | | | 324/207.25 |
| 9,109,973 B2* | 8/2015 | Inhoff | ................. | G01M 17/007 |
| 2010/0307240 A1* | 12/2010 | Tezuka | .................... | G01P 3/443 |
| | | | | 73/494 |
| 2013/0026731 A1* | 1/2013 | Mikura | ............... | B60B 27/0068 |
| | | | | 280/279 |
| 2013/0239420 A1* | 9/2013 | Kroll | ................... | G01B 11/275 |
| | | | | 33/228 |

OTHER PUBLICATIONS

Written Opinion from the International Searching Authority for Application No. PCT/IB2014/001228 dated Nov. 18, 2014 (5 pages).

* cited by examiner

METHOD AND APPARATUS FOR CONDUCTING PHASED ARRAY TESTING

CROSS-REFERENCE TO RELATED APPLICATIONS

This application claims priority to U.S. Provisional Application No. 61/841,495, filed Jul. 1, 2013, the entire contents of which are incorporated herein by reference.

FIELD OF THE INVENTION

The present invention relates to the field of phased array testing. Specifically, the present invention relates to a method and apparatus for conducting phased array testing on an industrial vehicle hub.

Vehicle hubs, in particular large industrial vehicle hubs, are commonly subjected to heavy loads, fatigue, and stress that cause component failure (e.g., cracks or other flaws) to develop in the hubs. If not detected and addressed, these component failures compromise the stability and lifespan of the vehicle hub, the wheel on which the vehicle hub sits, and/or the vehicle itself.

Phased array testing is a non-destructive form of ultrasonic testing that includes the use of commercially available probes that emit high-resolution beams of sound into a component, producing an image or series of images representative of the inside of the component.

SUMMARY

In accordance with one construction of the invention, a system for conducting phased array testing on a vehicle hub includes a guide element having a first end and a second end, a pivot element extending from the second end to couple to the vehicle hub, and a slide element coupled to the guide element. The slide element is movable relative to the guide element between the first end of the guide element and the second end of the guide element. The slide element including an object-receiving aperture to receive a phased array probe element.

In accordance with another construction of the invention, a method for conducting phased array testing includes coupling an end of a guide element of a testing apparatus to a center of an industrial vehicle hub to be tested. The method also includes coupling a phased array probe element to a slide element that is slidably coupled to the guide element. The method also includes adjusting a radial position of the slide element relative to the center of the hub along the guide element, and rotating the guide element about the center of the hub.

Other aspects of the invention will become apparent by consideration of the detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited.

DETAILED DESCRIPTION

FIGS. 1-4 illustrate a phased array testing apparatus 10. The apparatus 10 is used in conjunction with phased array testing equipment to test for component failures (e.g., cracks or other flaws). In particular, the apparatus 10 is used to test for component failures in industrial vehicle hubs. Other uses of the apparatus include but are not limited to testing of commercial vehicle hubs and other components having radial dimensions.

With reference to FIGS. 1-5, the apparatus 10 includes a guide element 14 having an elongate configuration. The guide element 14 has a first end 18 and a second end 22. The first end 18 has a generally rounded shape, and the second end 22 has a generally rectangular shape. Other constructions of the guide element 14 include different shapes and configurations of the first and second ends 18, 22.

Figure 3:
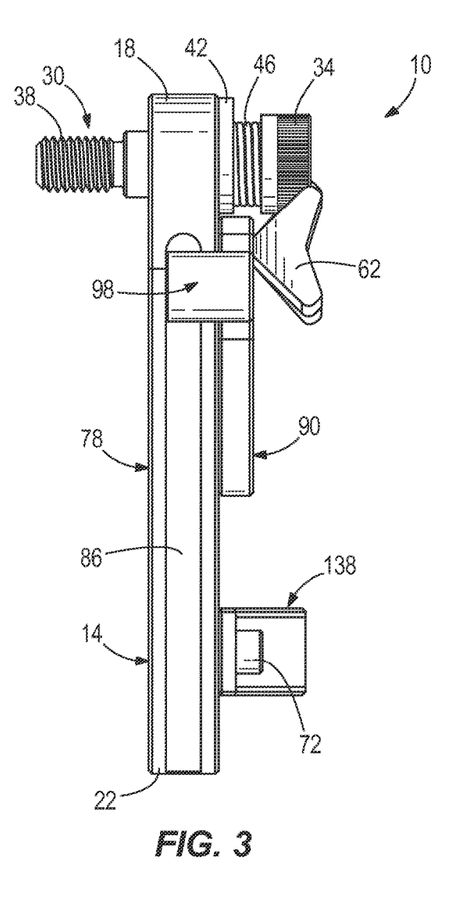
FIG. 3 is a right side view of the apparatus of FIG. 1.
Figures 4, 5:
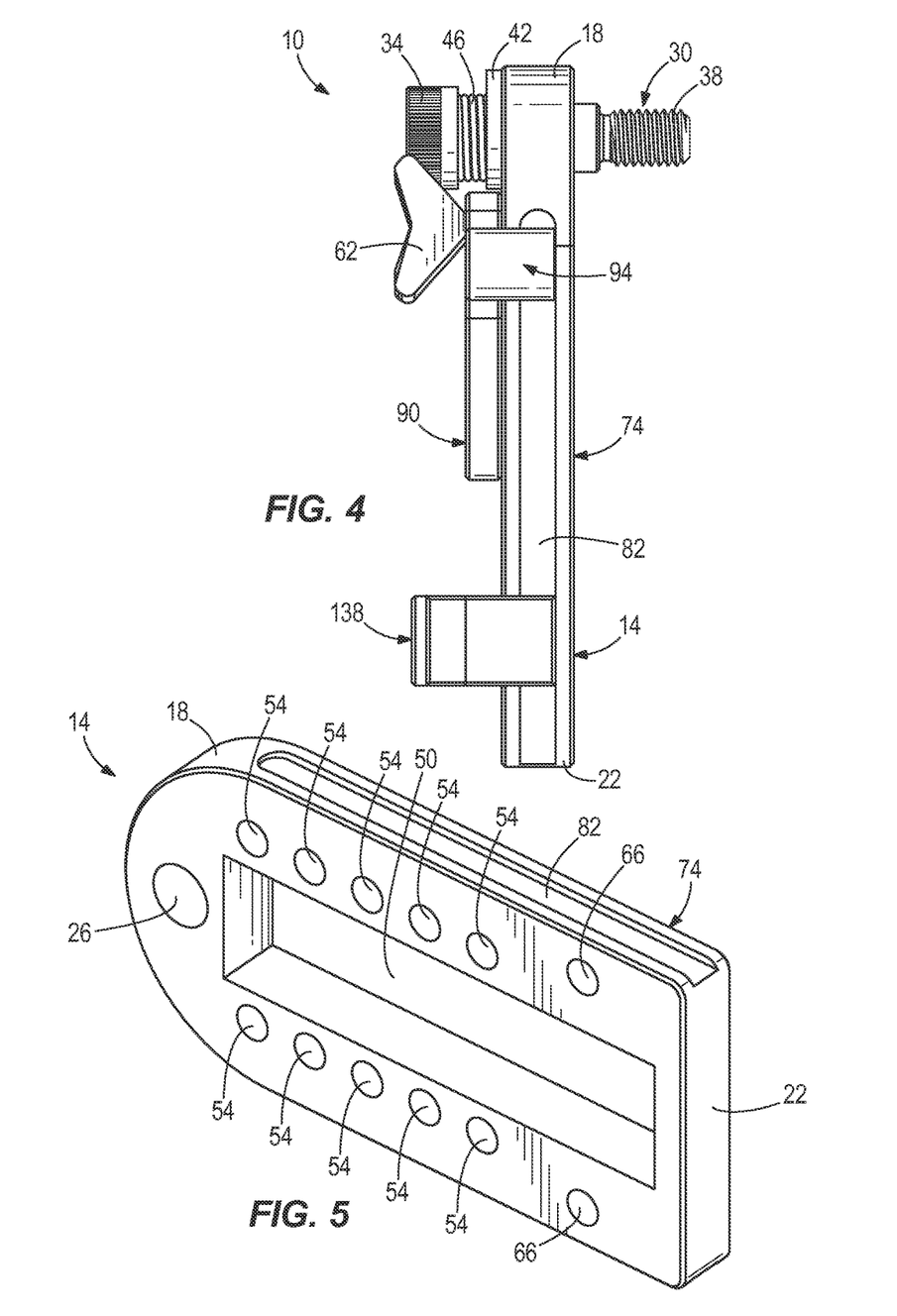
FIG. 4 is a left side view of the apparatus of FIG. 1.
FIG. 5 is a bottom perspective view of a guide element of the apparatus of FIG. 1.

With reference to FIG. 5, the first end 18 includes a pivot aperture 26. As illustrated in FIGS. 1-4, a pivot element 30 extends through the pivot aperture 26. The pivot element 30 is a threaded bolt having a head 34 and a threaded portion 38 extending from the head 34, though in other constructions the pivot element 30 is a pin or other structure that permits pivoting motion of the guide element 14 about the pivot element 30. The apparatus 10 further includes a washer 42 positioned about the pivot aperture 26, and a spring element 46 positioned between the washer 42 and the head 34. The spring element 46 extends around a portion of the pivot element 30, and biases the head 34 away from the washer 42 and the guide element 14.

With reference to FIG. 5, the guide element 14 includes a central slot 50 with an elongate configuration. The slot 50 extends entirely through the guide element 14. The guide element 14 further includes guide element positioning apertures 54 disposed on either side of the slot 50. Ten positioning apertures 54 in total are illustrated, five on either side of the slot 50. The positioning apertures 54 are spaced evenly apart from one another along each side of the slot 50, and form five pairs of positioning apertures 54 extending from the first end 18 to the second end 22. In other constructions different numbers and/or arrangements of the positioning apertures 54 are used.

Figure 1:
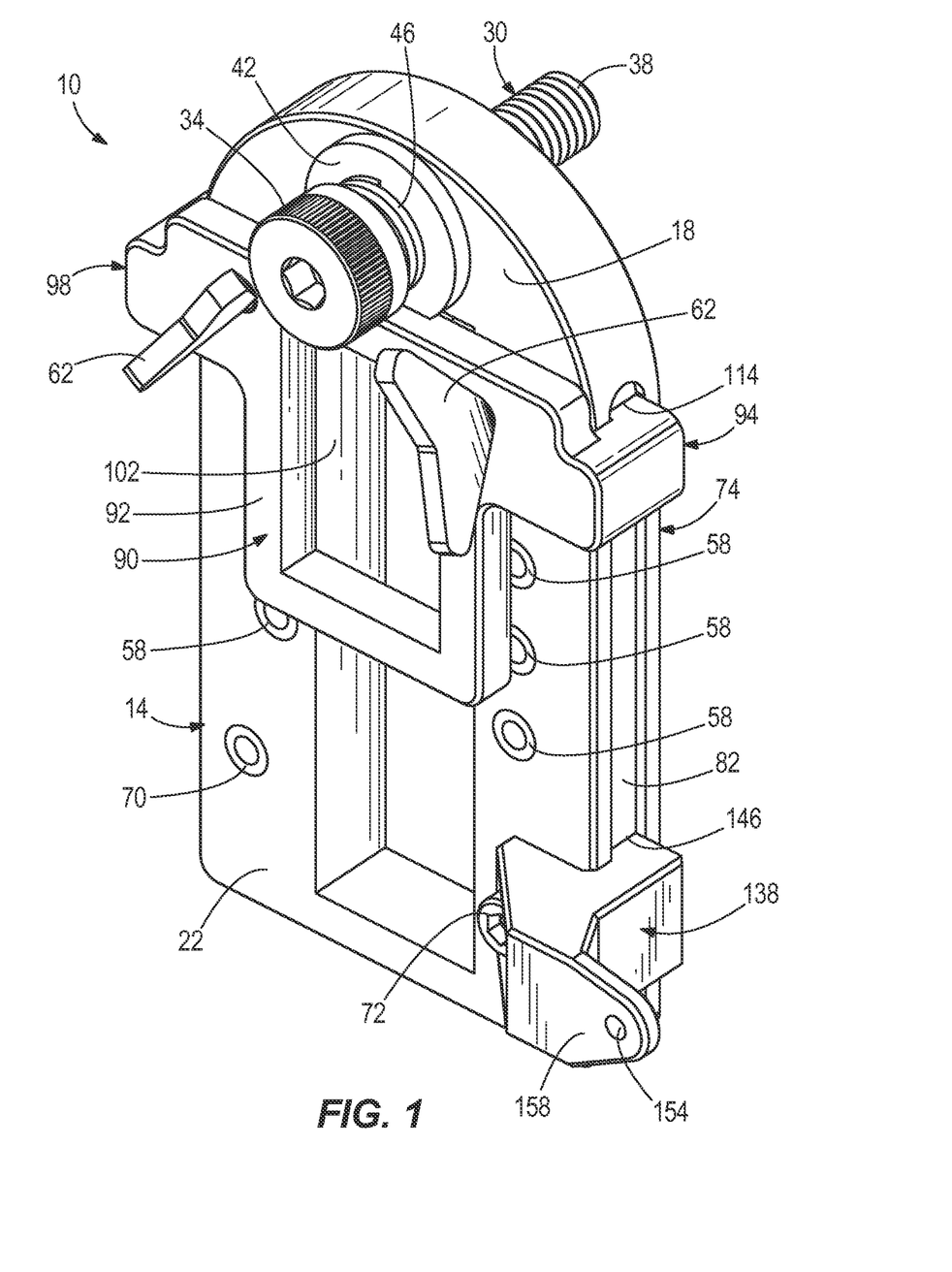
FIG. 1 is a top perspective view of an apparatus for use in conducting phased array testing.
Figure 2:
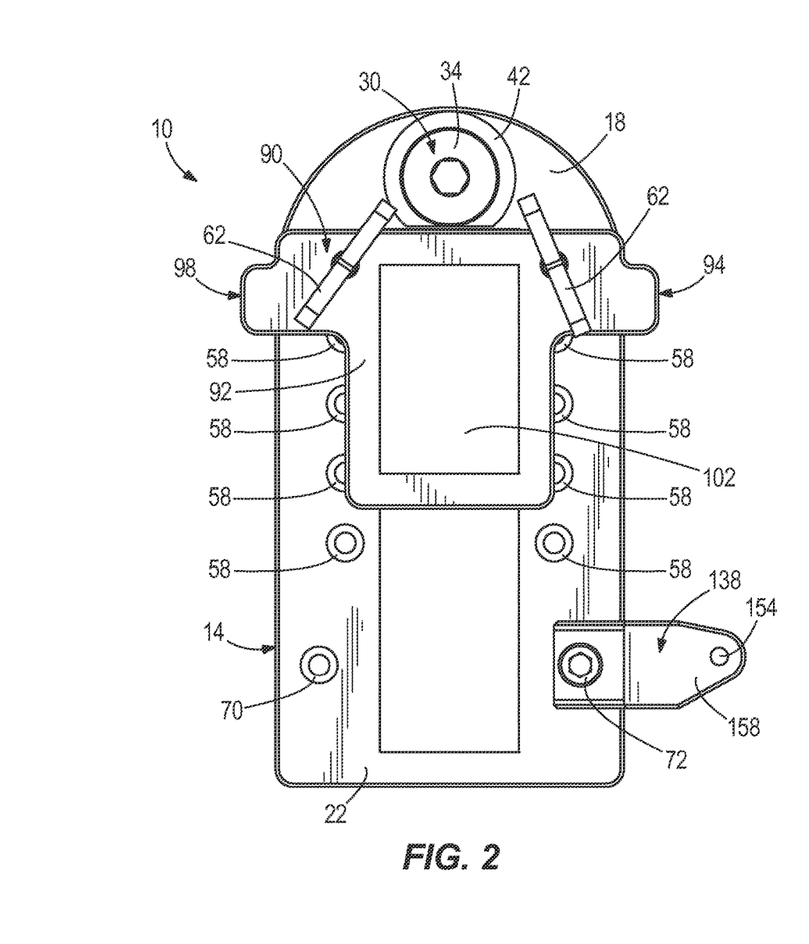
FIG. 2 is a top plan view of the apparatus of FIG. 1.

With reference to FIGS. 1 and 2, the apparatus 10 includes threaded inserts 58 positioned within the positioning apertures 54. The inserts 58 are threaded brass inserts. The inserts 58 are configured to receive threaded fastener elements 62. The threaded fastener elements 62 illustrated in FIGS. 1-4 are wing screws, though in other constructions different types of fastener elements 62 are used, including but not limited to bolts, other types of screws, etc.

With reference to FIG. 5, the guide element 14 further includes bracket receiving apertures 66. The apertures 66 are located on the second end 22. Two apertures 66 are illustrated, one on either side of the slot 50, though other constructions include different numbers and arrangements for the apertures 66. As illustrated in FIGS. 1 and 2, threaded inserts 70 are disposed within the apertures 66, similar to the inserts 58. The inserts 70 are configured to receive a threaded fastener element 72.

With reference to FIGS. 1 and 3-5, the guide element 14 includes a first side surface 74 extending between the first end 18 and the second end 22, and a second side surface 78 extending between the first end 18 and the second end 22. Located along the first side surface 74 is a first slot 82, and located along the second side surface 78 is a second slot 86. The slots 82, 86 each have an elongate configuration, and extend partially into the guide element 14.

With reference to FIGS. 1-4 and 6, the apparatus 10 further includes a slide element 90 releasably coupled to the guide element 14. The slide element 90 is movable relative to the guide element 14. The slide element 90 includes a main body portion 92, a first winged portion 94 extending outwardly from the body portion 92, and an oppositely opposed second winged portion 98 extending outwardly from the body portion 92. The main body portion 92 includes an object-receiving aperture 102 that extends through the slide element 10. In the illustrated construction the object-receiving aperture 102 is a slot. The object-receiving aperture 102 is configured to receive a piece of phased array testing equipment, as described further herein.

Figure 6:
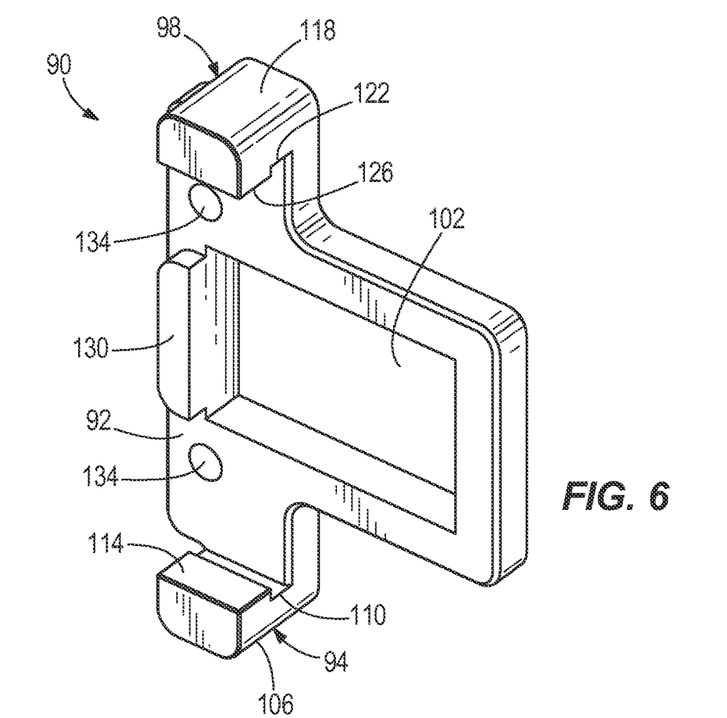
FIG. 6 is a bottom perspective view of a slide element of the apparatus of FIG. 1.

With reference to FIG. 6, the first winged portion 94 includes an arm 106 having a notched region 110 and an inwardly extending projection 114 adjacent the notched region 110. The second winged portion 98 includes an arm 118 having a notched region 122 and an inwardly extending projection 126 adjacent the notched region 122. As illustrated in FIGS. 1, 3, and 4, the projections 114, 126 extend into and are received by the slots 82, 86, respectively, on the guide element 14, such that the slide element 90 is restrained from movement relative to the guide element 14, other than a sliding movement along the slots 82, 86.

With continued reference to FIG. 6, the slide element 90 further includes a stop element 130. The stop element 130 is a projection adjacent one end of the object-receiving aperture 102. As illustrated in FIGS. 1-4, at least a portion of the stop element 130 sits within the slot 50 on the guide element 14 and limits translational sliding motion of the slide element 90 relative to the guide element 14.

With reference to FIG. 6, the slide element 90 further includes slide element alignment apertures 134, one on either side of the object-receiving aperture 102. Other configurations include different numbers and/or configurations of the alignment apertures 134. As the slide element 90 moves relative to the guide element 14 within the slots 82, 86, the alignment apertures 134 on the slide element 90 align with the positioning apertures 54 on the guide element 14. To lock a position of the sliding element 90 relative to the guide element 14, for example as seen in FIG. 1, the threaded fastener elements 62 (e.g., wing screws) are passed through both the alignment apertures 134 and the positioning apertures 54.

With reference to FIGS. 1-4 and 7, the apparatus 10 further includes a bracket 138. The bracket 138 is releasably coupled to the guide element 14. The bracket 138 includes a notched region 142 and a projection 146 adjacent the notched region 142. As illustrated in FIG. 1, the projection 146 extends into and is received by one of the slots 82, 86 on the guide element 14, such that the bracket 138 is movable along the slot 82 or 86, similar to the slide element 90.

Figure 7:
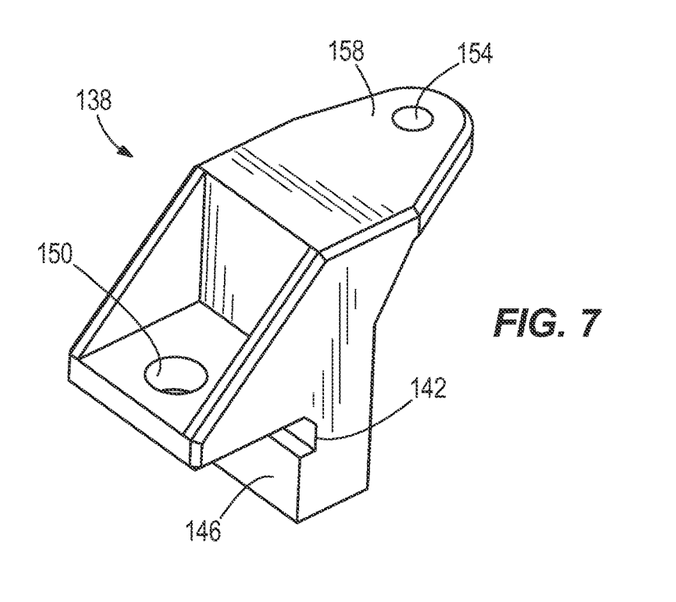
FIG. 7 is a top perspective view of a bracket of the apparatus of FIG. 1.

With continued reference to FIG. 7, the bracket 138 further includes a bracket attachment aperture 150. To lock a position of the bracket 138 relative to the guide element 14, for example as seen in FIG. 1, the aperture 150 is aligned with one of the apertures 66 on the guide element 14 and a threaded fastener element 72 is passed through both the aperture 150 and the aperture 66.

With reference to FIGS. 1, 2, and 7, the bracket 138 further includes an encoder-receiving aperture 154. The encoder-receiving aperture 154 is configured to receive an encoder, as further described herein. The encoder-receiving aperture 154 is located on a winged portion 158 of the bracket 138 that extends away from the guide element 14.

With reference to FIGS. 8-12, a phased array testing system 162 includes the apparatus 10, a phased array probe element 166 releasably coupled to the apparatus 10, an encoder element 170 releasably coupled to the apparatus 10, a main controller 174 (FIG. 10) releasably coupled to both the probe element 166 and the encoder element 170, and a calibration element 176. The phased array testing system 162 is used to test one or more vehicle hubs, such as an industrial vehicle hub on a large cask transporting device, for component failure.

With reference to FIGS. 1-12, the process of testing a vehicle hub 178 (FIG. 11) includes first applying a gelatinous couplant material on the hub 178. The process then includes coupling the first end 18 of the guide element 14 to a center of the hub 178 by inserting the pivot element 30 through the pivot aperture 26 and into a threaded aperture 180 (FIG. 11) in the center of the hub 178. With the guide element 14 coupled to the center of the hub 178, the guide element 14 is rotatable (e.g., up to 360 degrees) about the pivot element 30 and the center of the hub 178.

Figure 8:
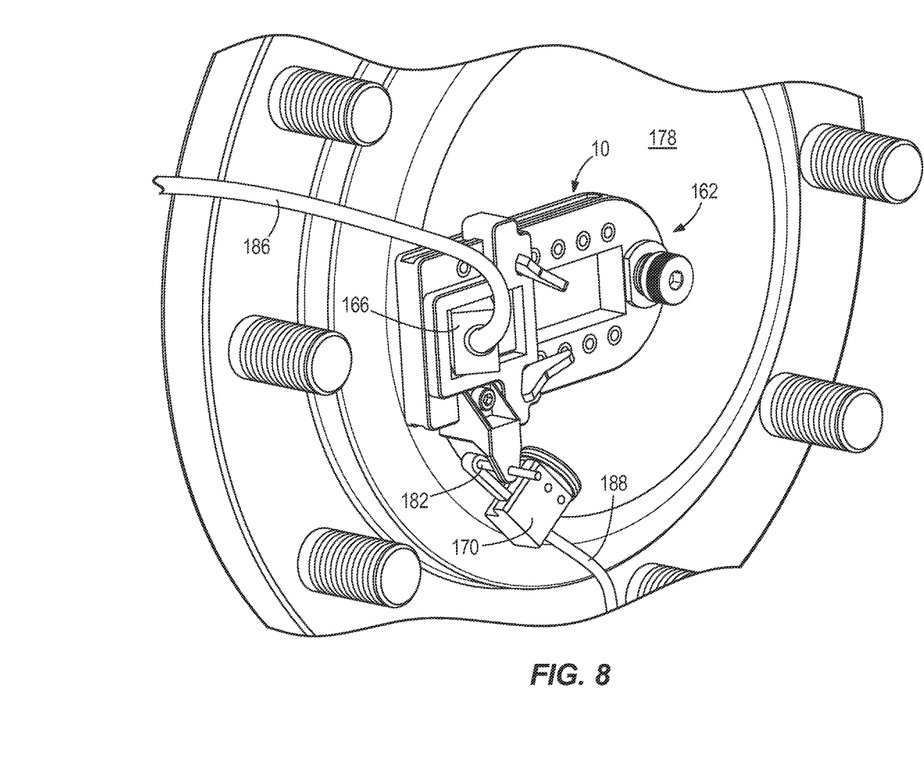
FIG. 8 is a perspective view of a phased array testing system including the apparatus of FIG. 1, the apparatus arranged in a first position.
Figure 9:
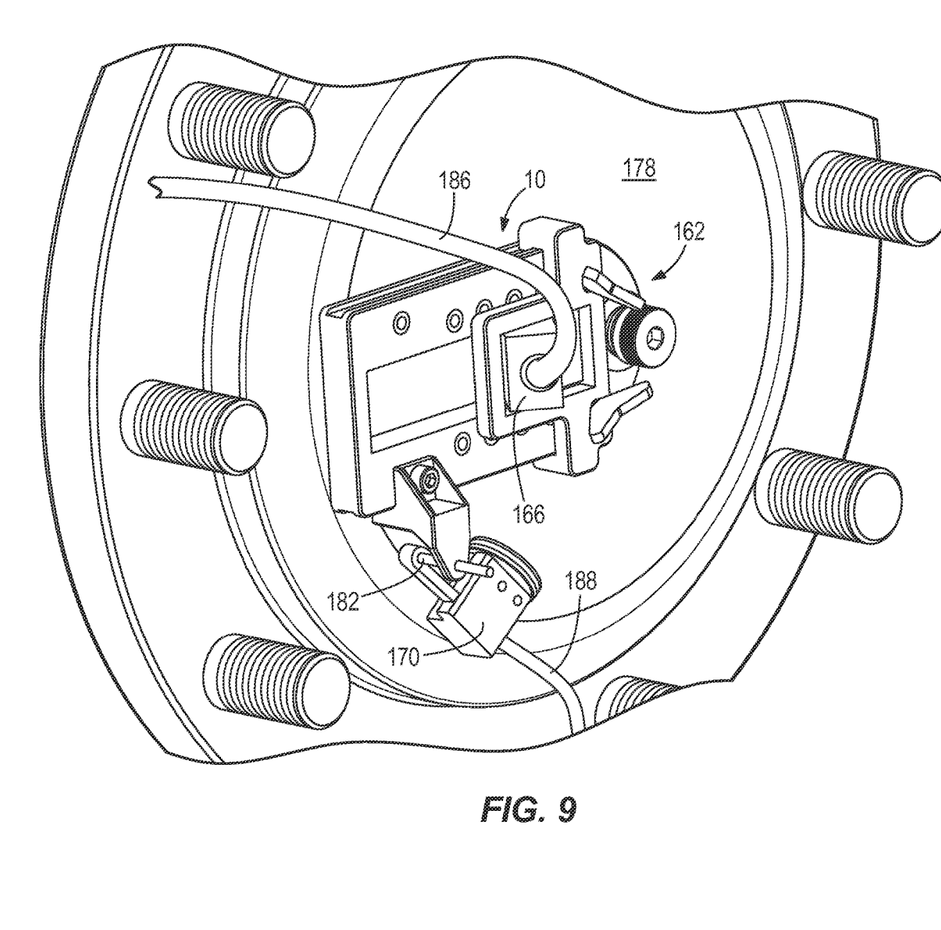
FIG. 9 is a perspective view of the system of FIG. 8, the apparatus arranged in a second position.

The process further includes releasably coupling the probe element 166 (e.g., a commercially available phased array wedge probe available from Olympus®, as illustrated in FIGS. 8 and 9) to the slide element 90 by inserting the probe element 166 into the object-receiving aperture 102 of the slide element 90. In some constructions the slide element 90 and/or the probe element 166 include additional components or structures (e.g., fasteners, clamps, etc.) to facilitate the coupling between the slide element 90 and the probe element 166. Coupling the probe element 166 to the slide element 90 may be done prior to or after coupling of the guide element 14 to the hub 178.

The process further includes releasably coupling the encoder element 170 (e.g., a commercially available mini-wheel encoder available from Olympus®, as illustrated in FIGS. 8 and 9) to the bracket 138 by inserting a rod 182 of the encoder element 170 through the encoder-receiving aperture 154. In some constructions, the slide element 90 and/or the encoder element 170 include additional components or structures (e.g., fasteners, clamps, etc.) to facilitate the coupling between the slide element 90 and the encoder element 170. Coupling the encoder element 170 to the bracket 138 may be done prior to or after coupling of the guide element 14 to the hub 178.

The process further includes releasably coupling both the probe element 166 and the encoder element 170 to the main controller 174 (e.g., a commercially available controller such as an OmniScan® MX available from Olympus®) with cables 186, 188 respectively. Coupling the cables 186, 188 to the main controller 174 may be done prior to or after coupling of the guide element 14 to the hub 178.

The process further includes turning on the main controller 174 and setting initial operating parameters. The initial operating parameters include, for example, setting a baseline (e.g., a reference Decibel level) on the main controller 174. Turning on the main controller 174 and setting the initial operating parameters may be done prior to or after coupling of the guide element 14 to the hub 178.

Figure 11:
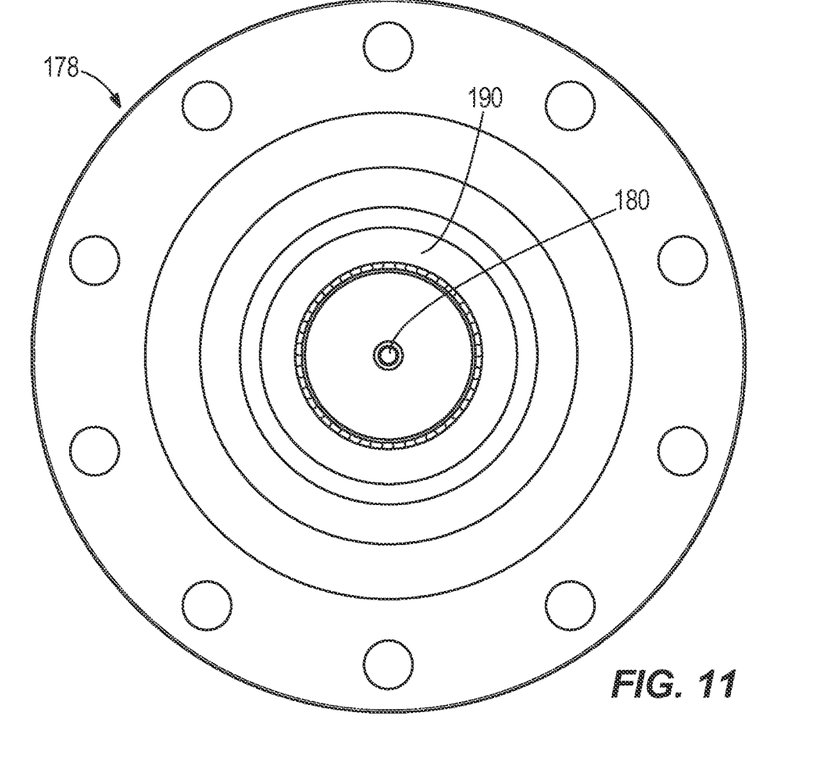
FIG. 11 is a diagram of a scanned hub area.

FIG. 11 illustrates an area 190 (darkened gray) to be scanned for component failures within the hub 178. In order to scan the entire area 190, the radial position of the slide element 90 and the coupled probe element 166 are adjusted relative to the center of the hub 178 during the testing. Specifically, the slide element 90 and probe element 166 are first moved to a position along the guide element 14 as illustrated in FIG. 8. With the slide element 90 and probe element 166 in the position illustrated in FIG. 8, the threaded fastener elements 62 are inserted through the alignment apertures 134 on the slide element 90 and the positioning apertures 54 on the guide element 14 to lock the slide element 90 relative to the guide element 14. The guide element 14 is then rotated about the center of the hub 178 (e.g., rotated 360 degrees manually by an operator), sweeping out a first area that is radially distant from the center of the hub 178. During this first sweep, and all other subsequent sweeps, the probe element 166 performs scans (e.g., raster scans) by emitting high-resolution beams of sound (e.g., at 9 Decibels above the baseline reference set in the initial operating parameters) into the hub 178. The probe element 166 scans for component failures within the hub 178. Simultaneously, the encoder element 170 facilitates positioning and dimensioning of the component failures within the hub 178.

With the initial sweep completed, the slide element 90 and the probe element 166 are then moved radially inward toward the center of the hub 178. Specifically, the threaded fastener elements 62 are removed from the alignment apertures 134 and the positioning apertures 54, and the slide element 90 is moved along the guide element 14 until the alignment apertures 134 align with a new set of positioning apertures 54 along the guide element 14. The threaded fastener elements 62 are then re-inserted through the alignment apertures 134 and into the new set of positioning apertures 54 to again lock the position of the slide element 90 and the probe element 166 relative to the guide element 14. With the slide element 90 and the probe element 166 locked in a new radial position relative to the center of the hub 178, the guide element 14 is again rotated about the center of the hub 178 (e.g., rotated 360 degrees manually by an operator), sweeping out a second area located radially interior to the first swept area.

In the illustrated construction, and with reference for example to FIG. 5, there are five radially spaced sets of positioning apertures 54 located along the guide element 14. The testing process involves moving the slide element 90 and the probe element 166 through each of five different radial positions corresponding to the five sets of positioning apertures 54. With each sweep of the guide element 14, an approximately 50% overlap in scanning occurs relative to the previous sweep. Thus, each new sweep of the guide element 14 causes the probe element 166 to scan at least a portion of the previously scanned area on the hub 178, ensuring that a full scan of the area 190 is obtained.

Figure 10:
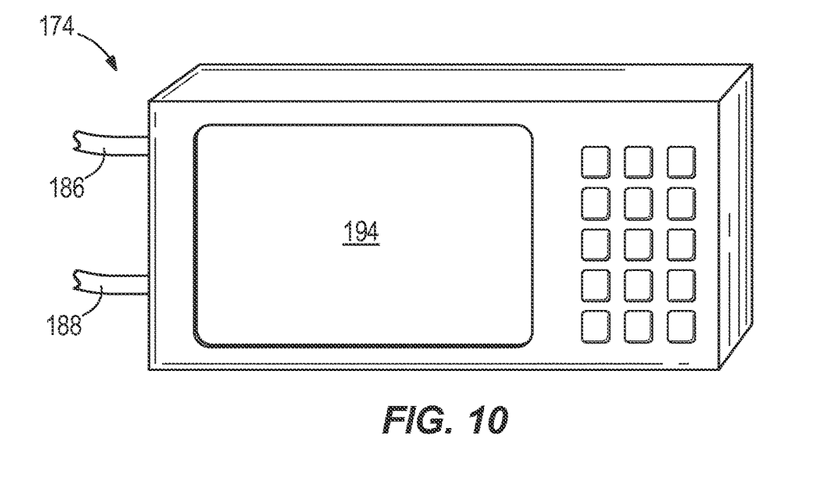
FIG. 10 is a schematic illustration of a main controller for use in the system of FIG. 8.

With reference to FIG. 10, during and/or after the scanning of the area 190, images of the hub 178 are displayed on a monitor 194 of the main controller 174. The main controller 174 uses software (e.g., TomoView™ software) to display the images and testing results. The images are representative of the interior of the hub 178, and provide indications of whether any component failures (e.g., cracks) exist within the hub 178. By reading and understanding the images, the operator (or other technician) then determines whether the hub 178 is defective and/or needs maintenance or replacement.

While the process of testing the hub 178 described above includes utilizing five different radial positions and an approximately 50% overlap for the slide element 90 and the probe element 166, in other constructions different numbers of radial positions and/or overlaps are utilized. For example, in some constructions the hub 178 is smaller than that shown, and only three radial positions are used to test hub 178. In some constructions, one or more sets of positioning apertures 54 are skipped over as the slide element 90 and the probe element 166 are moved along the guide element 14. For example, in some constructions the slide element 90 and the probe element 166 are moved initially from a radially outer set of positioning apertures 54 (as seen in FIG. 8) directly to a radially inner set of positioning apertures 54 (as seen in FIG. 9), skipping over the positioning apertures 54 in between. In some constructions, the guide element 14 includes more than five sets of radially spaced positioning apertures 54. In some constrictions the overlap used during the process is between approximately 40% and 60%. In some constructions the overlap is between approximately 45% and 55%.

With the hub 178 fully tested, the process further includes removing the guide element 14 from the hub 178 and coupling the guide element 14 to another hub (not shown) to be tested. To remove the guide element 14, the pivot element 30 is removed from the center of the hub 178. During both removal and attachment of the guide element 14 to another hub, the slide element 90, the probe element 166, and the encoder element 170 remain coupled to the guide element 14. Thus, the entire system 162 is easily movable from one hub to another hub to test each hub on a vehicle or vehicles, without any significant assembly or disassembly between testing.

Figure 12:
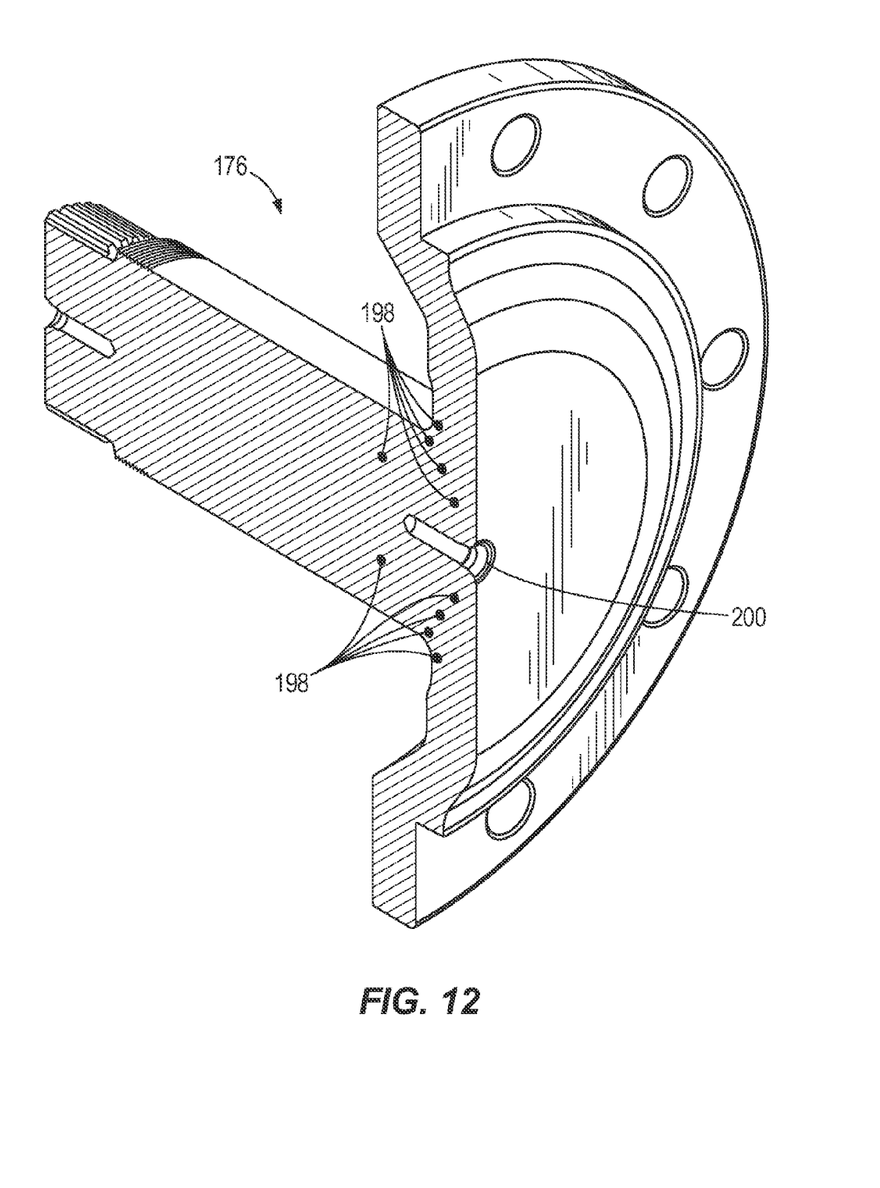
FIG. 12 is a perspective view of a calibration unit for use in the system of FIG. 8.

With reference to FIG. 12, and as described above, the system 162 includes a calibration element 176. Prior to testing the hub 178, the calibration element 176 is used to calibrate the probe element 166. The calibration element 176 resembles approximately half of a hub (e.g., hub 178), though other constructions include different shapes and configurations. The calibration element 176 includes a predetermined set of one or more component failures 198. In the illustrated construction, the component failures 198 are ten small drilled apertures of various depths extending into the calibration element 176 and spaced at various locations along the calibration element 176. In some constructions the calibration element 176 includes a different number, arrangement, type, or size of the component failures 198.

The step of calibrating the probe element 166 includes testing the calibration element 176 for component failures, similar to the method described above for testing hub 178. Specifically, the pivot element 30 is coupled to a threaded aperture 200 on the calibration element 176. The probe element 166 is then moved along the calibration element 176 (e.g., with the apparatus 10), and scans for the component failures 198. The probe element 166 is calibrated to an exact depth, sensing area, and flaw (crack) size for each of the known component failures 198, thereby creating a baseline calibration for accurately measuring actual component failures in real vehicle hubs (or other structures).

During the calibration process, the probe element 166 is also calibrated for dead element verification (i.e., verification of missing lines of data), velocity, delay, sensitivity, and time controlled gain. The baseline reference Decibel level, as described above, is also established during the calibration process, and is used during subsequent testing of hub 178 or additional hubs or structures.

Although the invention has been described in detail with reference to certain preferred embodiments, variations and modifications exist within the scope and spirit of one or more independent aspects of the invention as described.

The invention claimed is:

1. A system for conducting phased array testing on a vehicle hub comprising:
a guide element having a first end and a second end spaced from the first end along a first axis;
a pivot element extending from the second end along a second axis to couple to the vehicle hub, the second axis extending perpendicular to the first axis, wherein the guide element is pivotally coupled to the pivot element about the second axis; and
a slide element coupled to the guide element, the slide element movable relative to the guide element along the first axis between the first end of the guide element and the second end of the guide element both before and after testing of the vehicle hub so as to adjust a position of the slide element relative to the guide element, the slide element including an object-receiving aperture to receive a phased array probe element.

2. The system of claim 1, wherein the system further includes a hub having a threaded center hole, and wherein the pivot element extends through an aperture in the second end of the guide element and into the threaded center hole to releasably and rotatably couple the guide element to the hub.

3. The system of claim 2, wherein the guide element and the slide element are both rotatable 360 degrees about the second axis.

4. The system of claim 1, wherein the guide element includes positioning apertures and the slide element includes an alignment aperture that aligns with the positioning apertures on the guide element as the slide element is moved relative to the guide element.

5. The system of claim 4, wherein the system further includes a threaded fastener element that extends through one of the positioning apertures on the guide element and the alignment aperture on the slide element to lock relative movement of the guide element and the slide element.

6. The system of claim 1, wherein the slide element includes a first winged portion and a second winged portion extending outwardly from a main body portion of the slide element, each of the first and second winged portions including a notched region.

7. The system of claim 6, wherein the first and the second winged portions include inwardly extending protrusions.

8. The system of claim 7, wherein the guide element includes side surfaces having slots that receive the inwardly extending protrusions.

9. The system of claim 1, wherein the system further includes a bracket releasably coupled to the guide element.

10. The system of claim 9, wherein the bracket includes a notched region and a protruding region adjacent the notched region, the protruding region received by a slot in the guide element.

11. The system of claim 9, wherein the bracket includes an encoder-receiving aperture to receive an encoder element.

12. The system of claim 1, further including a calibration component having at least one component failure embedded therein, wherein the guide element is configured to be coupled to the calibration component to test the calibration component.

13. The system of claim 1, wherein the guide element includes an elongate slot that extends entirely through the guide element.

14. The system of claim 13, wherein the elongate slot is centrally located on the guide element.

15. The system of claim 13, wherein the slide element is a single piece element that includes a protruding stop that extends into the elongate slot, wherein the stop limits translational sliding motion of the slide element relative to the guide element.

16. The system of claim 1, wherein the guide element includes a pivot aperture, and wherein the pivot element extends through the pivot aperture.

17. The system of claim 1, wherein the object-receiving aperture extends entirely through the slide element.

18. The system of claim 2, further comprising a phased array probe element coupled to the slide element, wherein the phased array probe element is disposed at least partially within the object-receiving aperture.

19. The system of claim 2, wherein the pivot element is a threaded bolt.

20. The system of claim 2, wherein the hub includes an axis of rotation, wherein the pivot element extends along the axis of rotation, and wherein the slide element is movable relative to the guide element between the first end of the guide element and the second end of the guide element along a direction that is perpendicular to the axis of rotation.

* * * * *